United States Patent

Stradella

[11] Patent Number: 6,099,503
[45] Date of Patent: Aug. 8, 2000

[54] RELOADABLE AUTO-INJECTOR

[75] Inventor: Giuseppe Stradella, Camogli, Italy

[73] Assignee: TEBRO, Luxembourg, Luxembourg

[21] Appl. No.: 08/930,189

[22] PCT Filed: Oct. 14, 1996

[86] PCT No.: PCT/EP96/01603

§ 371 Date: Jul. 16, 1998

§ 102(e) Date: Jul. 16, 1998

[87] PCT Pub. No.: WO96/32974

PCT Pub. Date: Oct. 24, 1996

[30] Foreign Application Priority Data

Apr. 18, 1995 [FR] France .................................. 95 04579

[51] Int. Cl.[7] ...................................................... A61M 5/20
[52] U.S. Cl. ........................... 604/135; 604/232; 604/131; 604/134
[58] Field of Search ..................... 604/218, 131, 604/134, 135, 136, 156, 157, 232, 207.9, 200, 211, 220, 224, 167

[56] References Cited

U.S. PATENT DOCUMENTS 5,092,042   3/1992   Bechtold et al. ...................... 604/135

FOREIGN PATENT DOCUMENTS 666084     9/1953   European Pat. Off. .
2654938    5/1991   France .
902776     5/1993   Germany .
WO9411041  5/1994   WIPO .

Primary Examiner—Ronald Stright, Jr.
Assistant Examiner—Jeremy Thissell
Attorney, Agent, or Firm—Sughrue, Mion, Zinn, Macpeak & Seas, PLLC

[57] ABSTRACT

A reloadable auto-injector including a housing portion (1, 101) designed to receive a syringe (3), and a cover portion (2, 102), the auto-injector incorporating an injection device for automatically injecting the substance contained in the syringe, the injection device comprising: a piston (21) comprising a high portion (21b) and a low portion (21c), the low portion (21c) co-operating with the plunger of the syringe, the piston (21) being mounted to move, under the effect of an actuating spring (22) between a cocked position and an end-of-stroke position, the spring (22) being compressed in the cocked position; and trigger means (19) mounted to move between a blocking position in which they hold the piston (21) in its cocked position, and a releasing position in which they release the piston (21), the trigger means (19) being released from their blocking position by an actuating member; the auto-injector being characterized in that it further includes recocking means for recocking the automatic injection device, the recocking means being organized to be actuated by the operation of opening and/or closing said cover portion (2, 102) of the auto-injector.

16 Claims, 11 Drawing Sheets

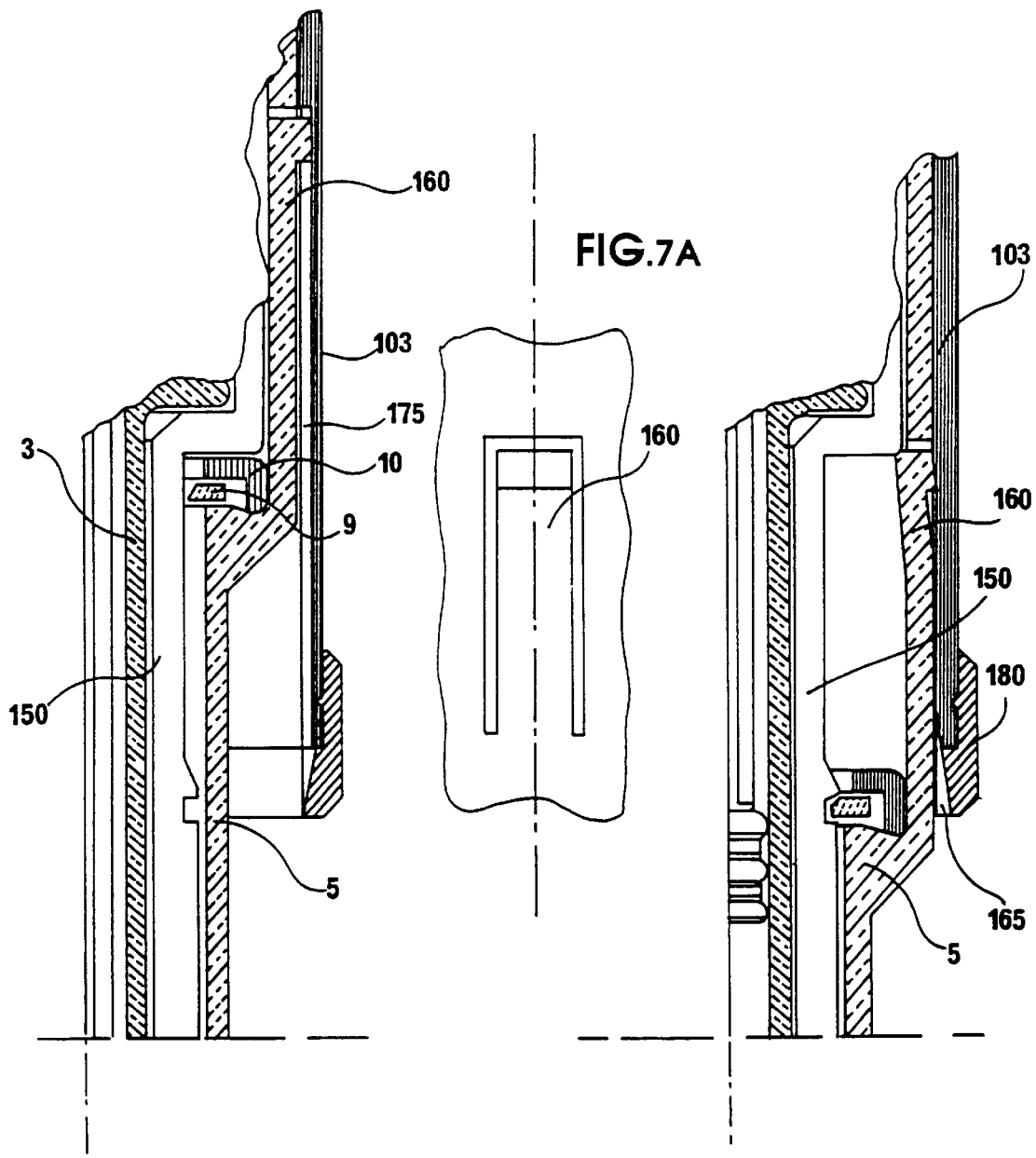

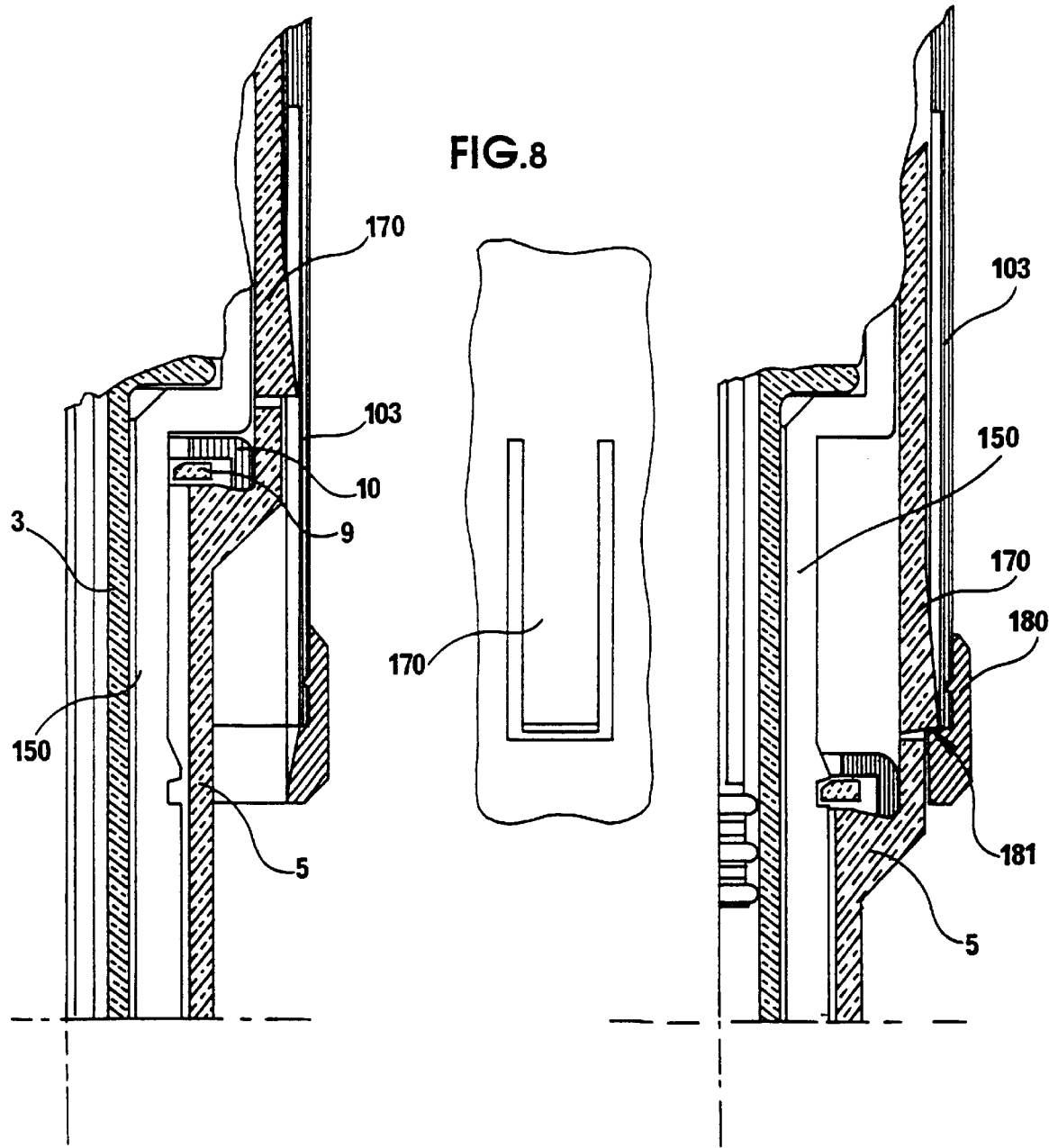

RELOADABLE AUTO-INJECTOR

The present invention relates to a reloadable auto-injector, i.e. an instrument enabling the contents of a syringe to be injected automatically into the body of a patient.

In the pharmaceutical field, automatic injection devices or "auto-injectors" have been developed to facilitate dispensing some kinds of medication by means of a syringe.

An example of such an auto-injector is disclosed in Document WO 94/11041. That instrument incorporates a first device for causing the needle to penetrate automatically into the body of the patient, and a second device for automatically injecting the substance, the second device being actuated only after the needle has penetrated fully into the body of the patient.

As with most of the current auto-injectors, a drawback with that instrument is that it is a disposable system designed to be used once only.

Unfortunately, for ecological but also economic reasons, a need has appeared for reloadable auto-injectors enabling the same instrument to be re-used several times.

Various reloadable devices have been developed to meet this need, but they all have the particularities of being relatively expensive, of being quite complicated to use, and of sometimes only partially solving the problem of disposing of waste and of protecting the environment.

The main drawback with using such a reloadable auto-injector lies in that it is complex to operate as compared with a disposable auto-injector. Because all auto-injectors are actuated by compressed springs, it is necessary to perform several operations before the instrument can be re-used. It is necessary to open the instrument, to reprime or to recock the spring, to replace the empty syringe with a new syringe, and then to close the instrument. Those steps are often quite complex, and they are generally performed by unscrewing that portion of the auto-injector which carries the syringe, by recompressing the spring by means of a separate tool, or by means of a slide actuated by the user and acting on said spring, then by screwing back on the syringe-carrying portion of the auto-injector after the syringe has been replaced. In certain existing devices, the entire syringe-carrying portion of the auto-injector is replaced.

The various above-mentioned steps for recocking existing instruments are often too complicated for many users, and they can give rise to the auto-injector not being used properly, which can have potentially dangerous results for the patient, or else it can reduce the effect of the treatment.

Document DE-90 27 776 discloses a reloadable automatic injection instrument. That instrument includes a device for causing the needle to penetrate, which device comprises a spring that initially displaces the needle inside the instrument towards the skin of the patient, and a device for injecting the substance, in which device the same spring then displaces a plunger inside a tank containing the substance. The instrument is actuated by a push-button.

That instrument suffers from several drawbacks. It is complicated and expensive to manufacture and to assemble because of the high number of constituent parts. Furthermore, its device for causing the needle to penetrate involves displacing the needle inside the instrument under the effect of said spring. The disadvantage of that way of implementing such a device is that it makes the effectiveness of needle penetration (the needle preferably penetrating to the fullest extent) depend on the stiffness of the spring. Unfortunately, once the needle has penetrated, the spring must still be sufficiently tensioned to inject the substance. Recocking that spring is thus quite difficult and tedious, particularly for people who are weak. In addition, since that instrument is actuated by a push-button, there is a risk of the instrument being actuated accidentally, e.g. before it has been positioned against the body of the patient in the desired place.

It therefore appeared advantageous to the Applicant to develop an auto-injector of the reloadable type that does not suffer from the above-mentioned drawbacks, but rather that offers the advantages of being cheap to manufacture, and extremely easy, simple, and reliable to operate, with respect both to actuating it and to recocking it.

The present invention thus provides a reloadable auto-injector including a housing portion designed to receive a syringe, and a cover portion, said auto-injector incorporating an injection device for automatically injecting the substance contained in the syringe, said injection device comprising:

a piston comprising a high portion and a low portion, said low portion co-operating with the plunger of the syringe, said piston being mounted to move, under the effect of an actuating spring between a cocked position and an end-of-stroke position, said spring being compressed in said cocked position; and trigger means mounted to move between a blocking position in which they hold the piston in its cocked position, and a releasing position in which they release the piston, said trigger means being released from their blocking position by an actuating member;

said auto-injector being characterized in that it further includes recocking means for recocking the automatic injection device, said recocking means being organized to be actuated by the operation of opening and/or closing said cover portion of the auto-injector.

The auto-injector of the invention thus offers the advantage of eliminating the step in which the spring of the automatic injection device is recocked, since this is achieved simultaneously with the displacement of the cover.

Preferably, a control sleeve is provided mounted to move between a locking position in which it holds the trigger means in their blocking position and thus the piston in its cocked position and an unlocking position in which said trigger means come into their releasing position in which they release the piston, said control sleeve being urged towards its locking position by a spring, and being forced into its unlocking position by said actuating member.

Advantageously, said trigger means are resilient, and they are provided with an interaction element co-operating on its inside with the high portion of the piston, and on its outside with the control sleeve, said interaction element holding said control sleeve in the unlocking position when said resilient trigger means are in their releasing position in which they release the piston, said high portion of the piston including a smaller-diameter portion which co-operates with said interaction element when the piston is in its cocked position, so that said resilient trigger means take up their blocking position in which they block said piston, thereby simultaneously releasing said control sleeve which takes up its locking position by coming into engagement around said interaction element of said resilient trigger means, thereby preventing said trigger means from returning to their releasing position in which the release the piston, the piston then being blocked in its cocked position.

In particular, the high portion of the piston comprises a hollow tubular cylinder whose outside surface co-operates with said interaction element of said resilient trigger means, that end of said tubular cylinder which is closer to the syringe being provided with a frustoconical portion forming the smaller-diameter portion of the piston, said tubular cylinder receiving an end of said spring for actuating the piston, the other end of said spring being secured to the housing of the auto-injector, so that, on opening and/or on closing the cover portion of the auto-injector, said tubular cylinder of the piston slides inside said trigger means, thereby entraining the spring so that it is compressed, until the smaller-diameter portion of the piston co-operates with the interaction element to block the piston in its cocked position.

In the first variant, said trigger means are implemented in the form of at least one resilient tab, and said interaction element is implemented in the form of a lug disposed at the free end of said resilient tab, said at least one resilient tab being brought into its piston-releasing position whenever said control sleeve is forced into its unlocking position, and said at least one resilient tab being brought into its piston-blocking position under the effect of the force exerted by said control sleeve, whenever said interaction element co-operates with said smaller-diameter portion of said piston.

In a second variant, said trigger means comprise a split ring which takes up its piston-releasing position whenever the control sleeve is forced into its unlocking position, and which takes up its piston-blocking position whenever it co-operates with the smaller-diameter portion of said piston.

In a first embodiment of the invention, the auto-injector includes a cover portion that can be interfitted with the housing portion by being fitted thereon, the injection device for automatically injecting the substance contained in the syringe being disposed in the cover portion, said cover portion being interfitted with said housing portion on being closed bringing said piston into its cocked position and brining said trigger means into their blocking position.

Preferably, said cover portion, and said housing portion are generally cylindrical in shape, said cover portion interfitting axially with said housing portion, said housing portion including said recocking means which comprise a cocking member that co-operates with at least one element secured to the piston on axially fitting said cover portion onto said housing portion so as to bring said piston into its cocked position.

Advantageously, said piston slides inside a fixed sleeve in the cover portion, said fixed sleeve being provided with at least one axial slot enabling said at least one element secured to the piston to project radially outwards from said fixed sleeve, said cocking member in the housing portion coming into engagement around said fixed sleeve on fitting the cover portion onto the housing portion, thereby acting on said at least one element secured to the piston to bring said piston into its cocked position.

Advantageously, said cocking member is cylindrical and is provided with at least one axial slot to enable said at least one element secured to the piston to slide relative to said cocking member while the piston is being displaced from its cocked position to its end-of-stroke position, it being possible for said cocking member to be rotated about said fixed sleeve between a cocking angular position, in which it co-operates with said at least one element secured to the piston to cock said piston, and a releasing angular position, in which said at least one axial slot in the cocking member is disposed facing said at least one element secured to the piston.

Preferably, said housing portion includes a tube mounted to slide axially relative to said cocking member between a rest position in which it covers up the needle of the syringe and an actuating position in which it acts as an actuating member, its end further from the syringe releasing the trigger means for triggering the injection means, said tube being provided with blocking means which prevent the tube from being displaced axially on said cocking member when said cocking member is in its cocking angular position, and which enable said tube to be displaced axially thereon, when the cocking member is in its releasing angular position.

Advantageously, said blocking means on the tube are implemented in the form of a resilient blocking finger projecting outwards from said tube, said tube further including an abutment finger projecting outwards from said tube, which finger allows the housing portion to be separated from the cover portion only when the cocking member is in its releasing angular position.

In particular, the cover portion includes a cylindrical outer casing which interfits with the tube of the housing portion by fitting around said tube, the inside diameter of said outer casing being approximately identical to the outside diameter of said tube, so that said casing being interfitted with said tube forces said resilient blocking finger inwards so as to prevent the tube from being displaced axially relative to said cocking member, the open end of the casing being provided with an insertion notch for inserting said projecting blocking tab, said notch being disposed circumferentially such that the cocking member is disposed in its cocking angular position when the cover portion is interfitted with the housing portion, the inside surface of the casing being provided with at least one axial groove extending to said open end, said at least one groove being offset angularly relative to said notch so that said blocking tab penetrates into said at least one axial groove when said cocking member is in its releasing angular position.

Preferably the inside surface of said cocking member in the vicinity of the end thereof that co-operates with said at least one element secured to the piston is provided with a securing circumferential groove which is releasably snap-fastened, after the piston has been cocked, on a complementary circumferential rib provided on the fixed sleeve, said securing rib and groove securing the housing portion to the cover portion in releasable manner before and after the auto-injector is actuated, and fixing the housing portion to the cover portion in non-releasable manner while the auto-injector is being actuated, the end of the tube blocking said groove on said rib when said tube is in its actuating position.

This first embodiment of the reloadable auto-injector offers the following advantages:

it is extremely simple to use and to reload;
it requires the user to make only a very small number of movements to reload it after it has been used: opening by applying axial traction, changing the syringe or the entire housing portion, axial interfitting, and rotation;
it eliminates any risk of undesired or partial triggering;
it eliminates any possibility of incorrect handling; and
it eliminates any risk of the user being injured.

In a second embodiment of the invention, the auto-injector includes a cover mounted to slide between a closed position and an open position in which it uncovers the syringe while remaining secured to the housing, the piston of the automatic injection device being connected to said cover of the housing, said cover being fully opened bringing said piston into its cocked position, and said trigger means into their blocking position.

Such an auto-injector offers the advantage of not being separated into two distinct portions while the syringe is being replaced, thereby avoiding the risk of losing one of the constituent parts of the instrument. In addition, the cover is extremely simple to operate by sliding it on the housing, and it cannot be used improperly by the patient.

In the second embodiment of the invention, said recocking means comprise a telescopic element comprising an internal rod secured to the high portion of the piston and an external tube, said rod being mounted to slide inside said tube between two abutment positions corresponding respectively to the cocked position and to the end-of-stroke position of the piston, said rod being urged towards said cocked position of the piston by the spring, said external tube being united in fixed manner with the cover and sliding with said cover during opening thereof.

Advantageously, said external tube is fixed to the cover via its end that is further from the syringe, and is provided at its opposite end with abutment-forming retaining means which co-operate with complementary means situated at that end of the internal rod which is further from the syringe to define the end-of-stroke position of the piston, and to prevent the internal rod from being disunited from the external tube, and to enable the injection device to be recocked on opening the cover, this operation causing the tube to slide axially, and therefore causing said rod to slide axially, so that the piston is returned to its cocked position by compressing the spring until the trigger means take up their blocking position, and said control sleeve takes up its locking position.

In an variant, said retaining means on said external tube are implemented in the form of an annular projection projecting into the tube, and said complementary means on said internal rod are implemented in the form of an annular swelling projecting outwards from said rod, it being possible for said rod to slide in said tube until its external swelling co-operates with the internal projection on said tube.

Advantageously, a resilient member is provided urging said syringe slightly proud of the housing portion of the auto-injector when the cover portion is removed or open, thereby making said syringe easier to grasp. This configuration makes it very simple for the patient to replace a used syringe with a new syringe without there being any risk of the patient being injured.

Other characteristics and advantages of the present invention appear on reading the following detailed description of two particular embodiments of the invention given by way of non-limiting example and with reference to the accompanying drawings.

In the drawings:

FIG. 7a is a front detail view of the blocking finger of the first embodiment of the invention;

FIGS. 7b and 7c are fragmentary vertical section views of the blocking finger shown in FIG. 6, respectively before and after the auto-injector is actuated;

FIG. 8 is a front detail view of the abutment finger of the first embodiment of the invention;

FIGS. 9a and 9b are fragmentary vertical section views of the abutment finger shown in FIG. 8, respectively before and after the auto-injector is actuated;

Figure 11:
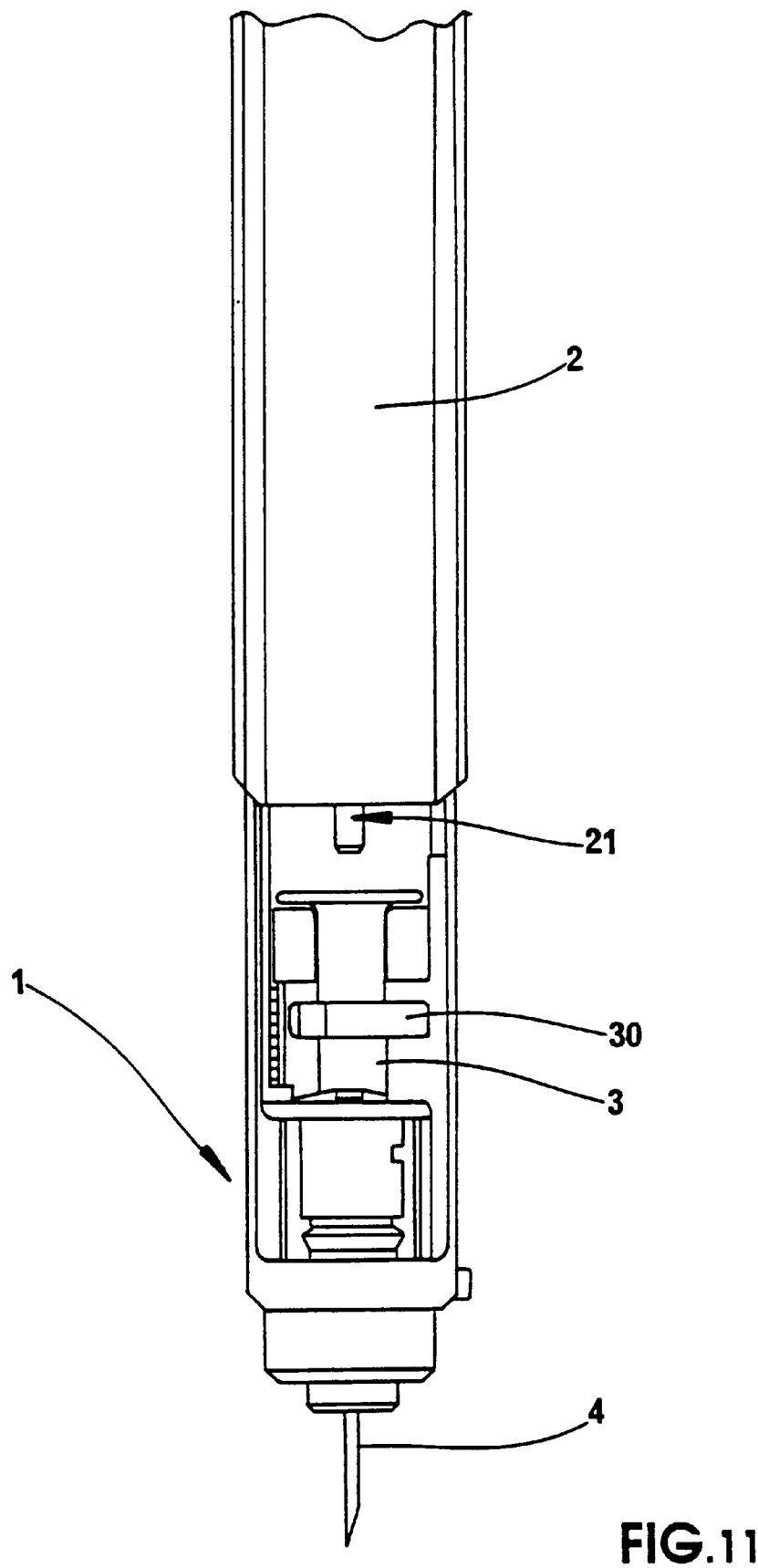
FIG. 11 is a fragmentary diagrammatic vertical section view of a second embodiment of an auto-injector of the present invention, the cover being partially open.
Figure 12:
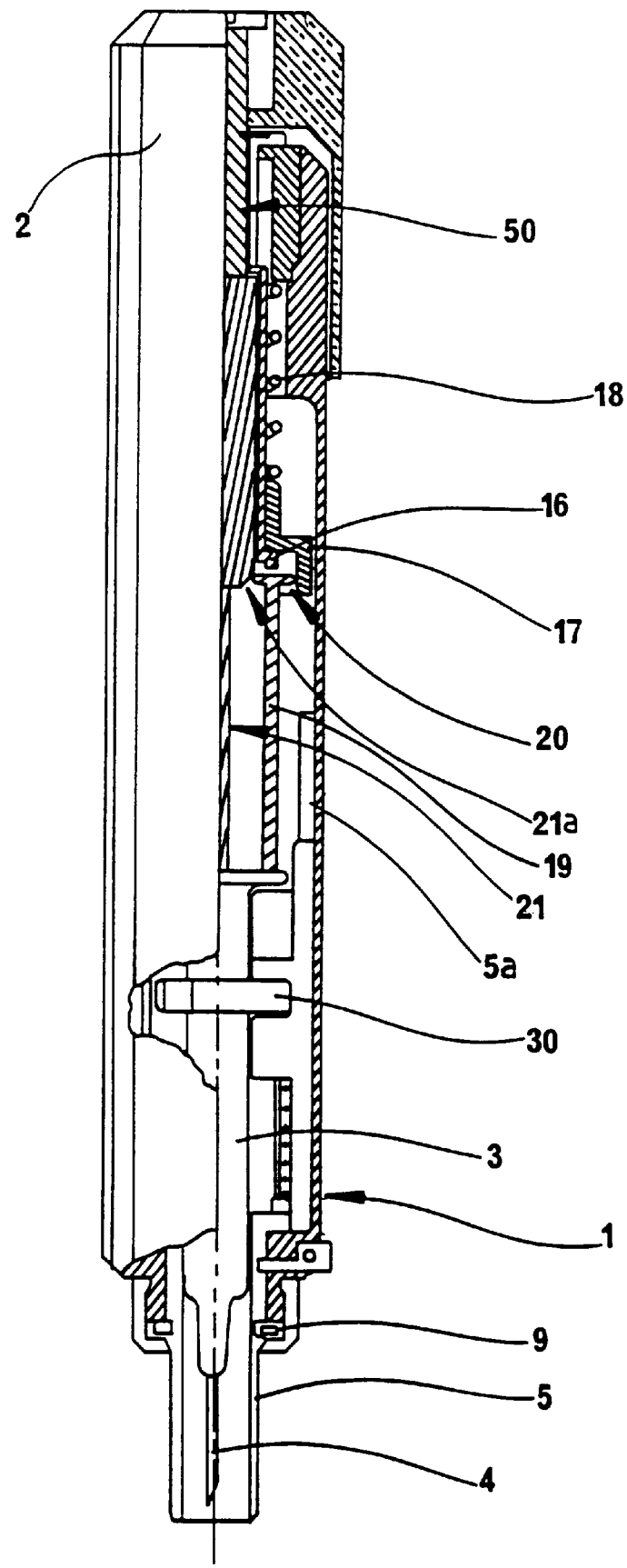
FIG. 12 is a vertical section view of a variant of the auto-injector shown in FIG. 11, the cover being closed and being shown only in part so as to show the internal structure.
Figure 14:
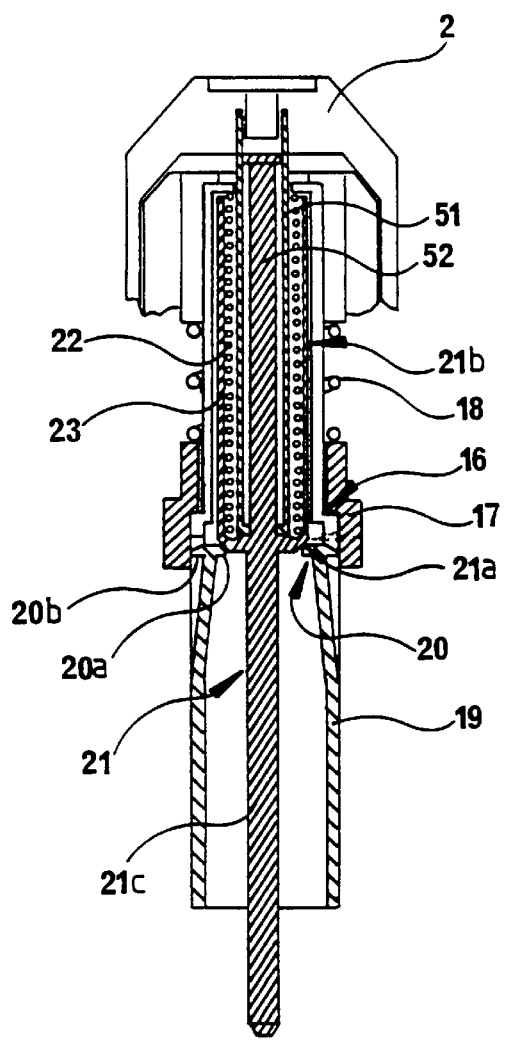
Figure 13:
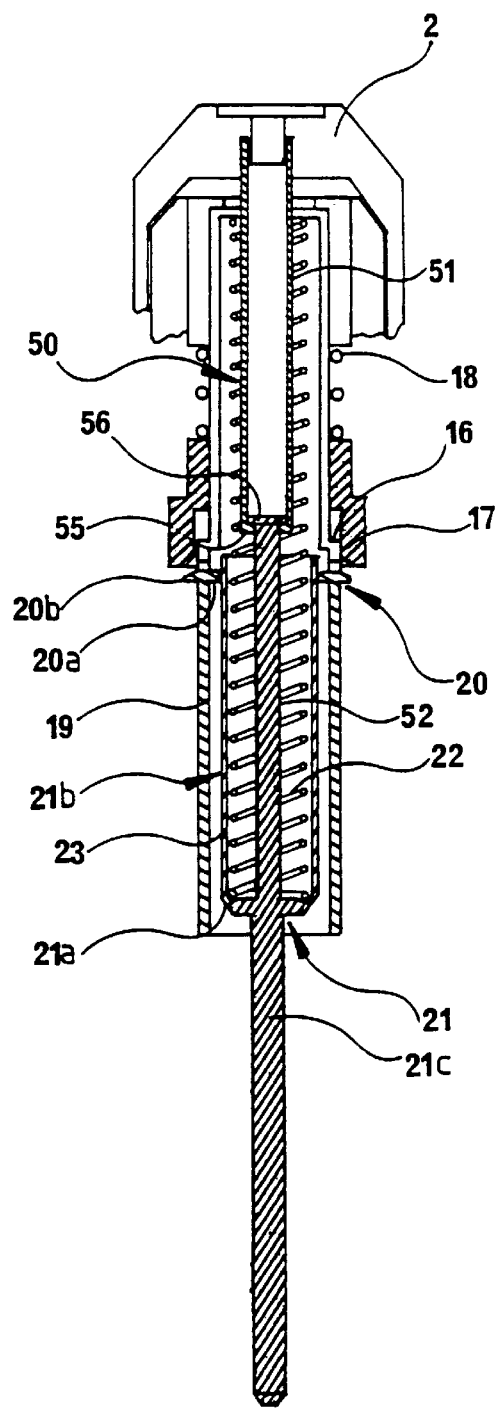
Figures 15A, 15B:
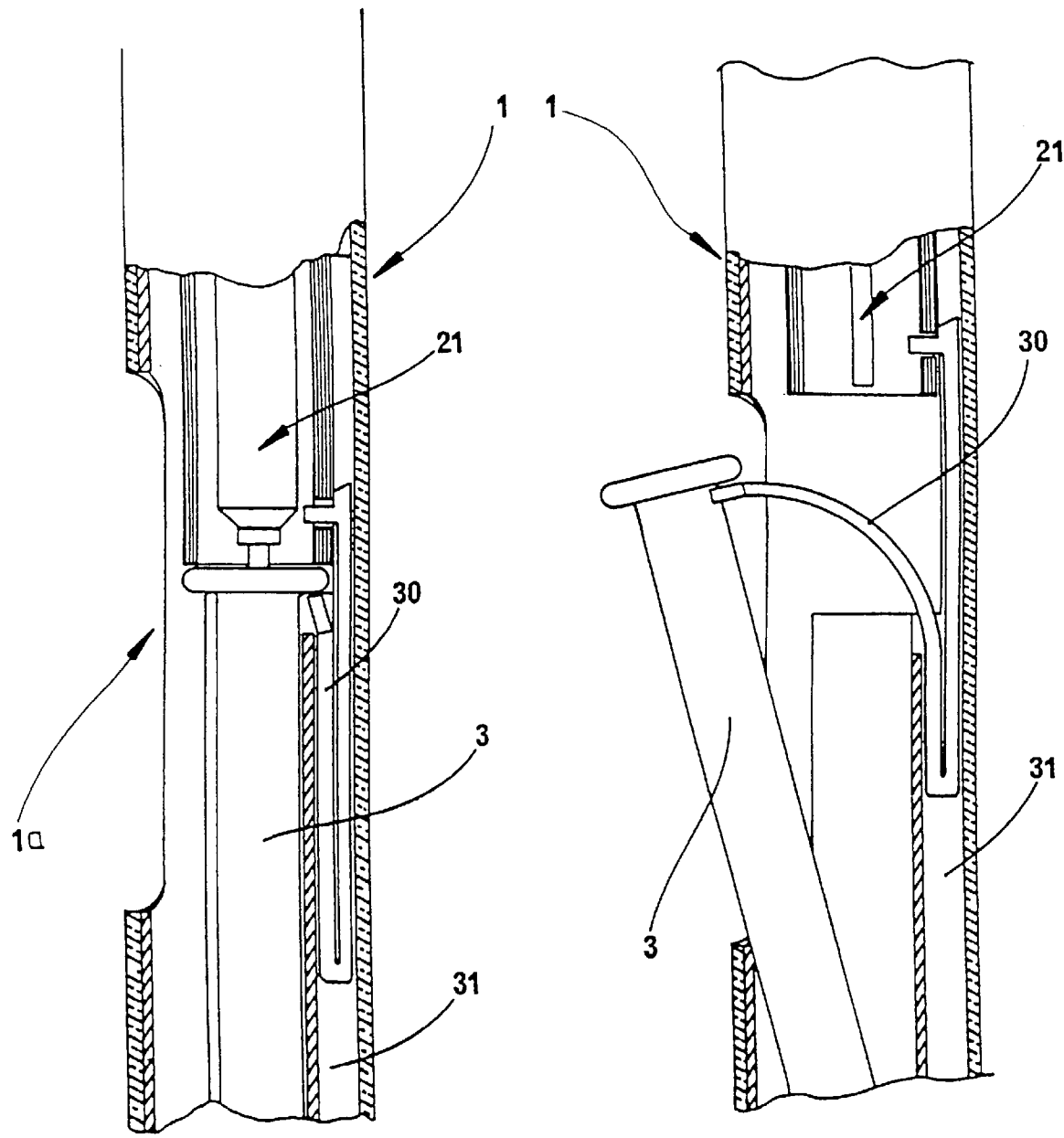

FIGS. 13 and 14 are vertical section views of the automatic injection device shown in FIGS. 11 and 12, and of the recocking means of the second embodiment of the auto-injector, respectively before and after the auto-injector is recocked; and FIGS. 15a and 15b are section views of a resilient member making it easier to change the syringe, with the cover portion respectively closed and open.

The invention concerns a reloadable auto-injector. The term "reloadable" is used to mean that the same auto-injector, i.e. an instrument incorporating an automatic injection device, can be used several times with different syringes that are generally of the "pre-filled" type, i.e. they are ready to use.

With reference to the figures, the auto-injector of the invention includes a syringe 3 which is received in the housing portion such that it is positioned in fixed manner. Advantageously, a resilient member 30 may be provided that acts on the syringe 3, e.g. a spring disposed under said syringe in the housing portion 1, 101, and urging said syringe slightly out of the housing portion when the cover portion 2, 102 is open or removed. Thus, after being used, the empty syringe projects slightly from its recess in the housing portion when the cover portion is open or removed, so that it is very easy to grasp for the purpose of replacing it.

The automatic injection device for automatically injecting the substance contained in the syringe corresponds substantially to that described in Document WO 94/11041. It includes a piston 21 co-operating with the plunger of the syringe (not shown), said piston 21 being mounted to move, under the effect of a spring 22 between a cocked position in which said spring 22 is compressed, and an end-of-stroke position. The piston 21 is held in its cocked position by trigger means 19 which are preferably resilient, and which advantageously include an interaction element 20. For example, they may be implemented in the form of at least one resilient tab 19 whose free end is provided with a lug 20. In which case, two resilient tabs 19 are preferably provided diametrically opposite from each other about the piston (see FIGS. 12, 13, and 14). Alternatively, said trigger means may also be implemented in the form a split ring (see FIGS. 1 to 5).

Said trigger means 19 are themselves mounted to move between a blocking position in which they hold the piston 21 in its cocked position, and a releasing position in which they release said piston 21.

A control sleeve 17 is also provided that is mounted to move between a locking position in which it holds the trigger means 19 in their blocking position and thus the piston 21 in its cocked position, and an unlocking position in which said control sleeve 17 no longer locks said trigger means 19 and in which said trigger means are brought into their piston-releasing position. The control sleeve 17 is urged into its locking position by a spring 18, and it is forced into its unlocking position by an actuating member. The actuating member may be arbitrary and may either be actuated directly by the user, or else be part of an automatic penetration device for causing the needle to penetrate automatically, as described in Document WO 94/11041 and as shown more precisely in FIGS. 1 to 3 and 12. In which case, a slidably mounted tube 5 is provided surrounding the needle 4 of the syringe 3, which tube 5 is applied against the skin of the patient, a sufficient force being necessary to enable said tube 5 to slide, said tube being initially retained by a member such as a split ring 9 so that, on pressing the auto-injector against the skin, a certain quantity of energy is stored up until said ring 9 moves out of the way under the effect of said force, said tube 5 then being able to slide relative to the needle of the syringe, thereby enabling said needle to penetrate into the body of the patient, full penetration of the needle being guaranteed by said energy stored up in the tube 5. In this embodiment, it is the end 5a of the tube 5 that comes into abutment at the end of the stroke against the control sleeve 17 and which then triggers automatic injection of the substance contained in the syringe. This guarantees that the substance is injected only once the needle has penetrated fully into the body of the patient.

The piston 21 comprises a high portion 21b and a low portion 21c. The low portion 21c is substantially in the form of rod, and it co-operates with the plunger of the syringe to inject the substance contained in the syringe into the body of the patient, while the piston 21 is being displaced from its cocked position to its end-of-stroke position under the effect of the actuating spring 22.

The high portion 21b of the piston 21 co-operates with said trigger means 19. As shown in FIGS. 1 to 5, the trigger means may be implemented in the form of a resilient split ring 19. This ring 19 co-operates firstly, on its inside 20a, with the high portion 21b of the piston 21a, and secondly, on its outside 20b, with the control sleeve 17. The high portion 21b of the piston 21 includes a smaller-diameter portion 21a which co-operates with said ring 19 when the piston 21 is in its cocked position. In this position, the control sleeve 17, as urged by its spring 18, comes into abutment against a shoulder 16 of the housing, and is then it its locking position in which it holds said ring 19 in its blocking position. The ring 19 is thus subjected to the force exerted by the spring 22 on the piston 21. When the actuating member forces the control sleeve 17 into its unlocking position, the split ring 19 is released on its outside 20b and it moves outwards at its split under the effect of said force exerted by the spring 22 and/or of its own resilience.

The piston 21 is then released and the substance contained in the syringe is injected into the patient. The split ring 19 is then in its piston-releasing position in which, via its outside 20b, it holds the control sleeve 17 in its unlocking position. Said split ring 19 is thus subjected to the force exerted by the spring 18 on the control sleeve 17. When the piston 21 comes back into its cocked position, and the split ring 19 once again faces the smaller-diameter portion 21a of the piston 21, it closes again inwards under the effect of said force exerted by the spring 18 and/or of its own resilience.

Advantageously, the high portion 21b of the piston 21 comprises a hollow tubular cylinder 23 whose outside surface co-operates with the inside 20a of said ring 19. The cylinder 23 receives one end of the actuating spring 22, and, at its end nearer the syringe, i.e. at its bottom end as shown in the figures, said cylinder is provided with a frustoconical portion forming said smaller-diameter portion 21a of the piston 21.

Implementing the smaller-diameter portion 21a of the piston 21 in the form of a frustoconical portion guarantees that said ring 19 slides progressively over said smaller-diameter portion 21a as it comes into or leaves its blocking position, thereby avoiding any risk of said ring 19 jamming in its blocking position.

Likewise, the control sleeve 17 may be provided in similar manner with a frustoconical portion in its portion that co-operates with said ring 19 so as to avoid any risk of said ring jamming in its releasing position in which it releases the piston 21.

In a first embodiment shown in FIGS. 1 to 10b, the auto-injector comprises a housing portion 101 and a cover portion 102 which may be disunited from said housing portion while changing syringes. The two portions making up the auto-injector are cylindrical with a directrix of the cylinder that is circular so as to enable the cover portion to rotate relative to the housing portion, as explained in more detail below in the description of how the first embodiment of the invention operates. The housing portion contains the syringe, while the cover portion contains the automatic injection device for automatically injecting the substance contained in said syringe.

In the first embodiment of the invention, the housing portion 101 receives and holds the syringe 3 in fixed manner. Advantageously, the syringe 3 is received in an approximately cylindrical part referred to below as the "cocking member" 150 whose recocking function whereby it recocks the injection device of the instrument is described below. In a first version, shown in particular in FIGS. 1 and 2, the syringe 3 is held in the cocking member 150 by means of a collar 6 abutting against a shoulder 151 on said member 150. In another version, shown in FIG. 3, the syringe 3 further includes one or more larger-diameter portions 7 which nest inside said cocking member 150.

The housing portion 101 comprises a hollow outer tube 5 disposed around said cocking member 150. Said tube 5 is mounted to be displaceable axially relative to said cocking member 150 between a rest position in which it covers up the needle 4 of the syringe 3 and an actuating position in which it uncovers said needle to enable it to penetrate into the body of the patient. However, the tube 5 cannot be displaced in rotation relative to the cocking member 150, so that rotating the housing portion 101, i.e. the tube 5, causes the cocking member 150 to be rotated identically.

Advantageously, a device such as a split ring 9 is provided between the tube 5 and the cocking member 150 in a groove so as to hold the tube 5 is its rest position, it only being necessary for a very small force to be applied to said tube to cause the split ring to come out of the groove, thereby enabling the tube 5 to be displaced towards its actuating position.

Figure 3:
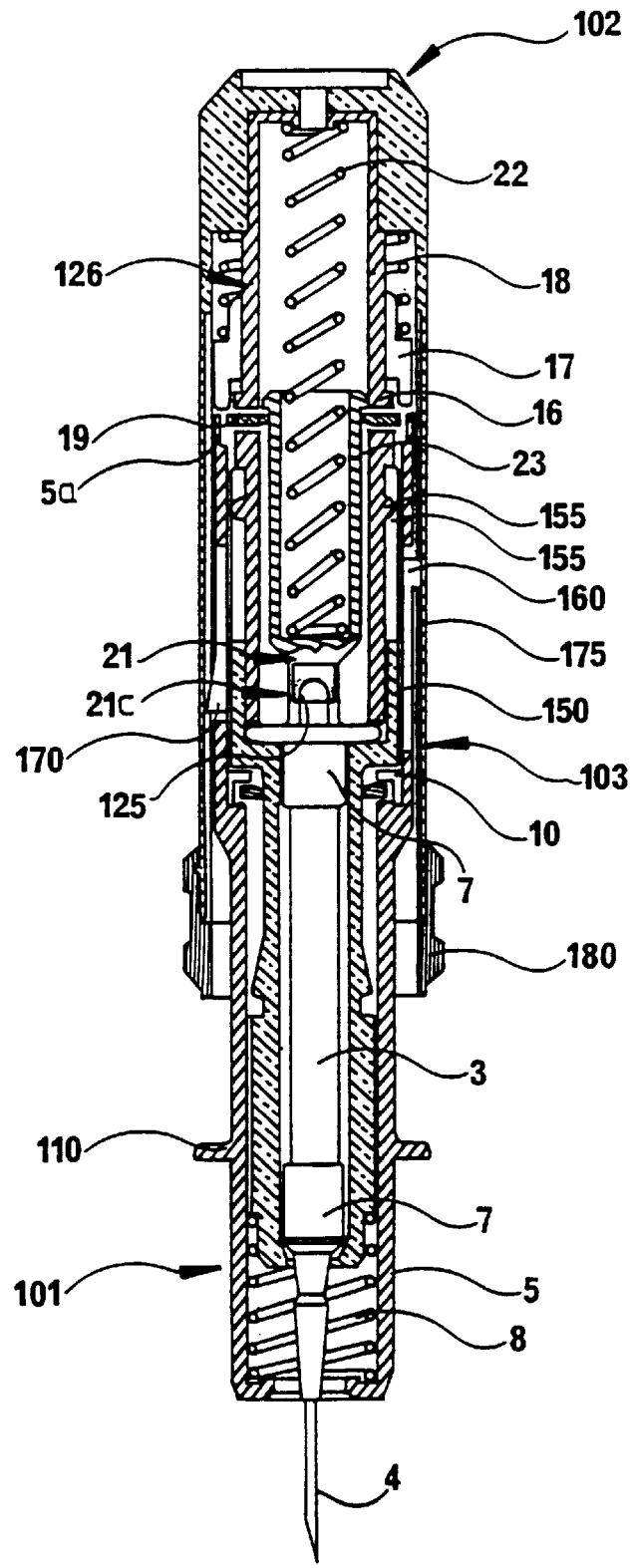
FIG. 3 is a vertical section view of a variant of the auto-injector shown in FIGS. 1 and 2, after the automatic injection device has been actuated.

It is thus guaranteed that the tube 5 is displaced until it reaches its actuating position, and thus that the needle penetrates fully into the body of the patient. When the tube 5 is in its actuating position, its end 5a acts on the sleeve 17, thereby releasing the injection device of the instrument, as described above. After the auto-injector has operated, the tube 5 is brought back towards its rest position so that firstly it covers up the needle of the syringe again, and secondly it enables the auto-injector to be used again. Advantageously, as shown in FIG. 3, a return spring 8 is provided to bring the tube back automatically into its rest position after the auto-injector has been used. In particular, this makes it possible to avoid risks of injury. To bring the split ring 9 back into its groove while the tube 5 is returning to its rest position, a returning member 10 is advantageously provided secured to said tube 5. Thus, the tube 5 is once again ready for the next time the auto-injector is used.

As shown in FIGS. 1 to 7, the tube 5 is provided with resilient blocking means 160 which may be implemented in the form of a resilient finger 160 mounted to move between a blocking position in which said finger is forced inwards and prevents the tube 5 from being displaced axially relative to the cocking member 150 and an unblocking position in which said finger projects outwards relative to the tube 5 and no longer prevents said tube 5 from being displaced axially on said cocking member 150. The blocking position of the finger 160 is shown in FIGS. 1, 4, 6, and 7b, and the unblocking position is shown in FIGS. 2, 3, 5, and 7c. The tube 5 is further provided with abutment means 170 which may be implemented in the form of a resilient abutment finger 170 projecting outwards relative to said tube 5. The functions of the blocking finger 160 and of the abutment finger 170 are described below.

Advantageously, said blocking finger 160 and said abutment finger 170 are disposed diametrically opposite each other on said tube 5.

At its end that is opposite from the needle 4 of the syringe 3, the cocking member 150 is provided with at least one axial slot 156. Preferably, the cocking member 150 is provided with two axial slots 156 disposed diametrically opposite each other about its central axis. The axial slots 156 serve to enable the auto-injector to be actuated, as described below.

The cover portion 102 of the first embodiment of the auto-injector of the invention comprises an outer casing 103 that is also cylindrical and that is configured so that it can fit onto the housing portion 101, and more particularly onto the tube 5. The inside diameter of the casing 103 is thus approximately identical to or very slightly larger than the outside diameter of said tube 5, so that the cover portion and the housing portion interfit snugly and with little friction.

At its open end, the outer casing 103 of the cover portion is provided with a notch 165, at which the inside diameter of said casing 103 is increased. Advantageously, the notch 165 has approximately the same width as said blocking finger 160 of the housing portion 101. Similarly, in the axial direction of the outer casing 103, going from the open end, the diameter of said notch preferably tapers until it is equal to the diameter of the casing 103 itself.

On its inside surface, the outer casing 103 is further provided with at least one groove 175 extending axially over a portion of the length of said casing 103, starting from its open end. Said at least one axial groove 175 serves to receive said blocking finger of the housing portion 101 to enable the auto-injector to be actuated. Advantageously, the outer casing 103 is provided with two diametrically opposite identical axial grooves 175.

According to the invention, said at least one axial groove 175 is offset circumferentially relative to said notch 165, preferably by about 90°.

Inside said casing 103, the cover portion 102 is provided with a hollow fixed sleeve 126 inside which the piston 21 is disposed, and which also contains the split ring 19 of the automatic injection device. The piston 21 is thus displaced axially inside said fixed sleeve 126 between its cocked position and its end-of-stroke position.

In the first embodiment of the invention, in its low portion 21c, the piston 21 includes at least one element 125 secured to the piston, and, for example, implemented in the form of a fin. Preferably two diametrically opposite fins 125 are provided as shown in particular in FIGS. 6, 10a, and 10b. The fins 125 project outwards relative to the fixed sleeve via respective axial slots 127 in said fixed sleeve 126. On displacing the piston 21 between its cocked position and its end-of-stroke position, said fins 125 are thus displaced accordingly in said axial slots 127.

The first embodiment of the auto-injector operates as follows.

The user of the auto-injector inserts a syringe 3 into the housing portion 101. Optionally, as shown in FIG. 3, the syringe 3 may be inseparable from the housing portion 101, in which case the user does not have to load the syringe into the housing portion.

The cover portion 102 containing the injection device is then engaged on the housing portion 101 so as to be interfitted therewith. Because of the blocking finger 160 projecting outwards from the tube 5 of the housing portion 101, the interfitting can be achieved only by inserting said blocking finger 160 into said notch 165 in the cover portion 102. The tapering of the diameter at the notch 165 forces said resilient blocking finger 160 inwards into its blocking position, as can be seen in particular in FIG. 7b. In this position, the blocking finger 160 is placed under a shoulder on the cocking member 150, thereby preventing said tube 5 from being displaced axially on said cocking member 150.

Figure 1:
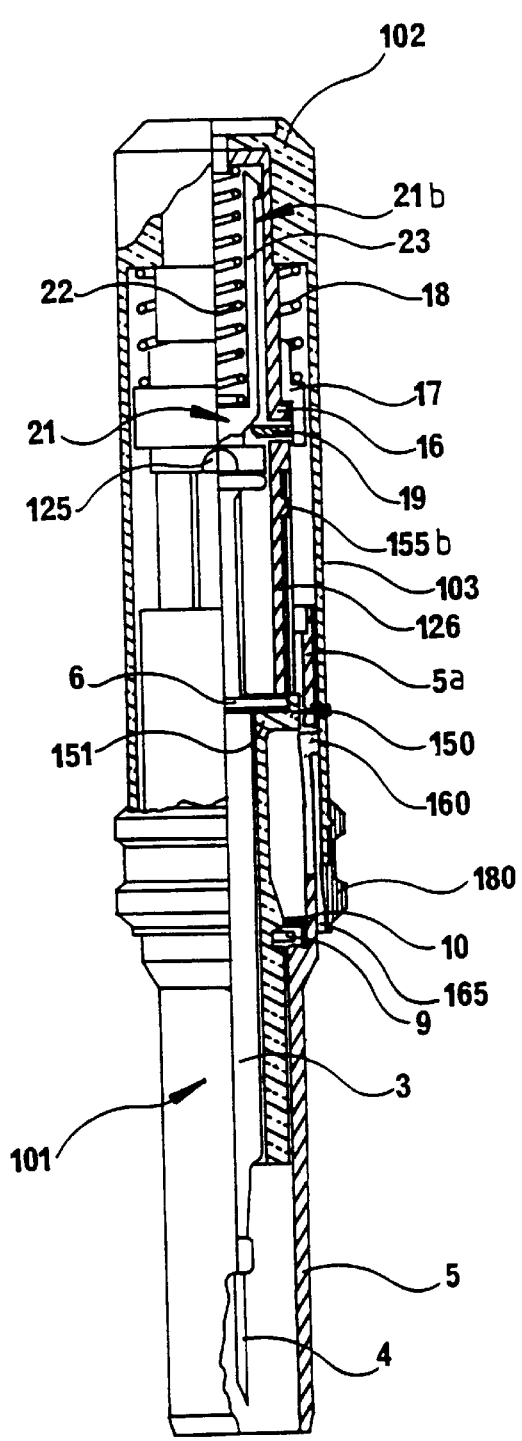
FIG. 1 is a fragmentary vertical section view of a first embodiment of the auto-injector of the invention, after the automatic injection device has been recocked.
Figures 4, 5:
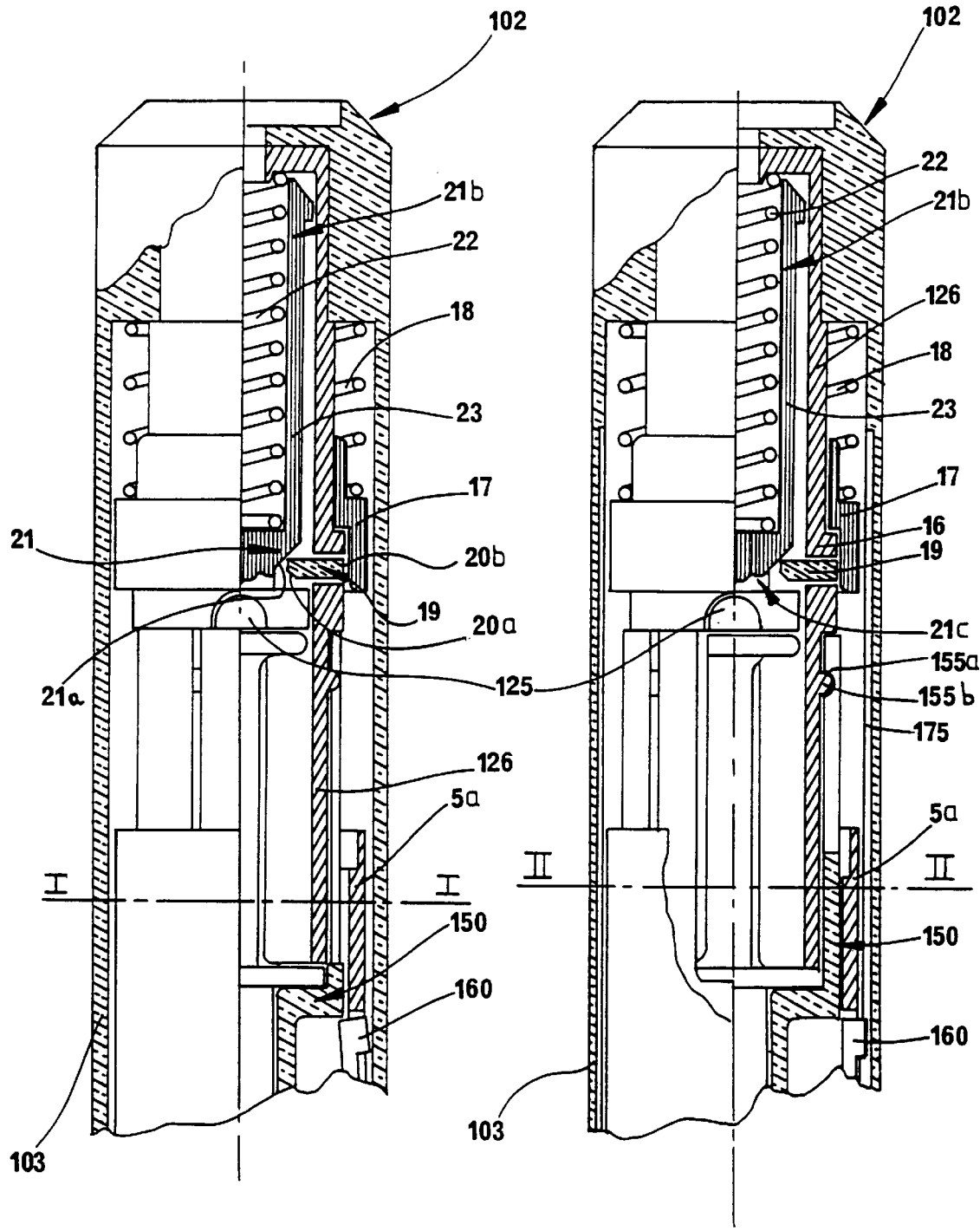
FIGS. 4 and 5 are enlarged views of the top portions respectively of FIGS. 1 and 2.
Figure 6:
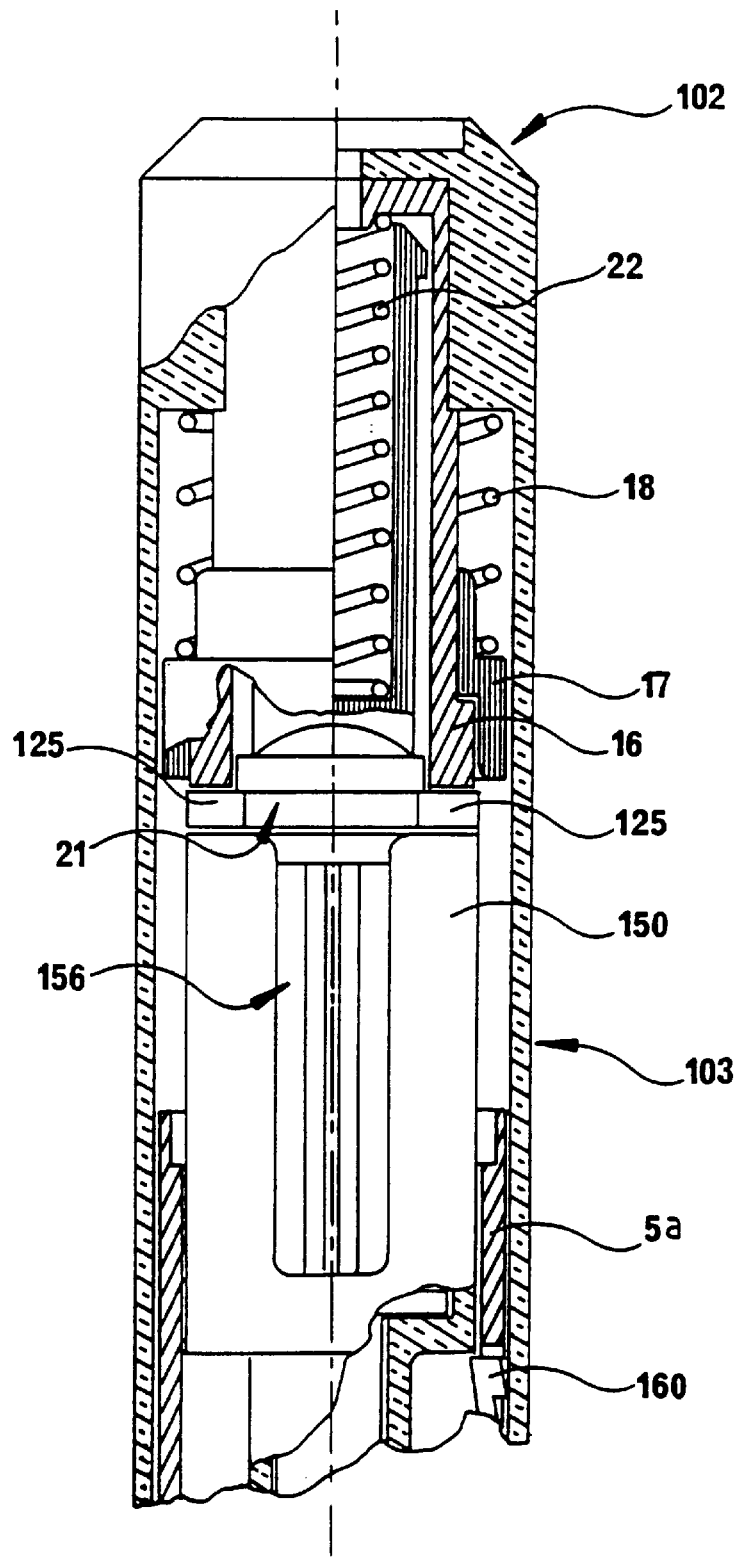
FIG. 6 is a view similar to the FIG. 4 view, the cover portion being rotated through 90° to show how the cocking member co-operates with the piston of the injection device.

The notch 165 is disposed circumferentially such that as shown in FIG. 6, when the cover portion 102 is interfitted with the housing portion 101, the top end of the cocking member 150 abuts against said fins 125 on the piston 21. Thus, by continuing to engage the cover portion onto the housing portion, the piston 21 is displaced towards its cocked position in which the injection device is cocked, as described above. The cocked position of the piston 21 is shown in FIGS. 1 and 4. In this position, the injection device cannot be actuated because of the blocking finger 160 which is in its blocking position.

During interfitting, the abutment finger 170 is also forced inwards so as to pass over and then come into abutment against a shoulder 181 of the casing 103, thereby preventing the housing portion 101 from being disunited from the cover portion 102. This abutment position is shown in FIG. 9a.

Optionally, at its open end, the casing 103 may include a separate part 180 which incorporates the notch 165 and the shoulder 181, and which is also provided with extensions to said axial grooves 175 in the casing 103.

When the housing portion 101 is interfitted with the cover portion 102, the cocking member 150 thus fits around the fixed sleeve 126. As shown in particular in FIGS. 4 and 5, the fixed sleeve 126 is provided with a circumferential rib 155b on which a corresponding groove 155a in the cocking member 150 is snap-fastened. This snap-fastening can be implemented because the cocking member is provided with at least one axial slot 156, and preferably two such slots, so that the snap-fastening is releasable relatively easily and merely enables the housing portion 101 to be minimally secured to the cover portion 102 before and after the auto-injector is actuated. Optionally, to facilitate this snap-fastening still further, one or more narrow additional axial slots may be provided in the cocking member 150. Similarly the rib 155b and its corresponding groove 155a advantageously have a rounded profile that facilitates snap-fastening and separation.

To actuate the auto-injector, it is necessary to rotate the housing portion 101 relative to the cover portion 102, thereby bringing the cocking member 150 from its cocking angular position to its releasing angular position. Advantageously, if the casing 103 is provided with two diametrically opposite axial grooves 175 offset by 90° relative to the notch 165, the rotation can be effected in both directions through an angle of about 90°.

Figure 10A:
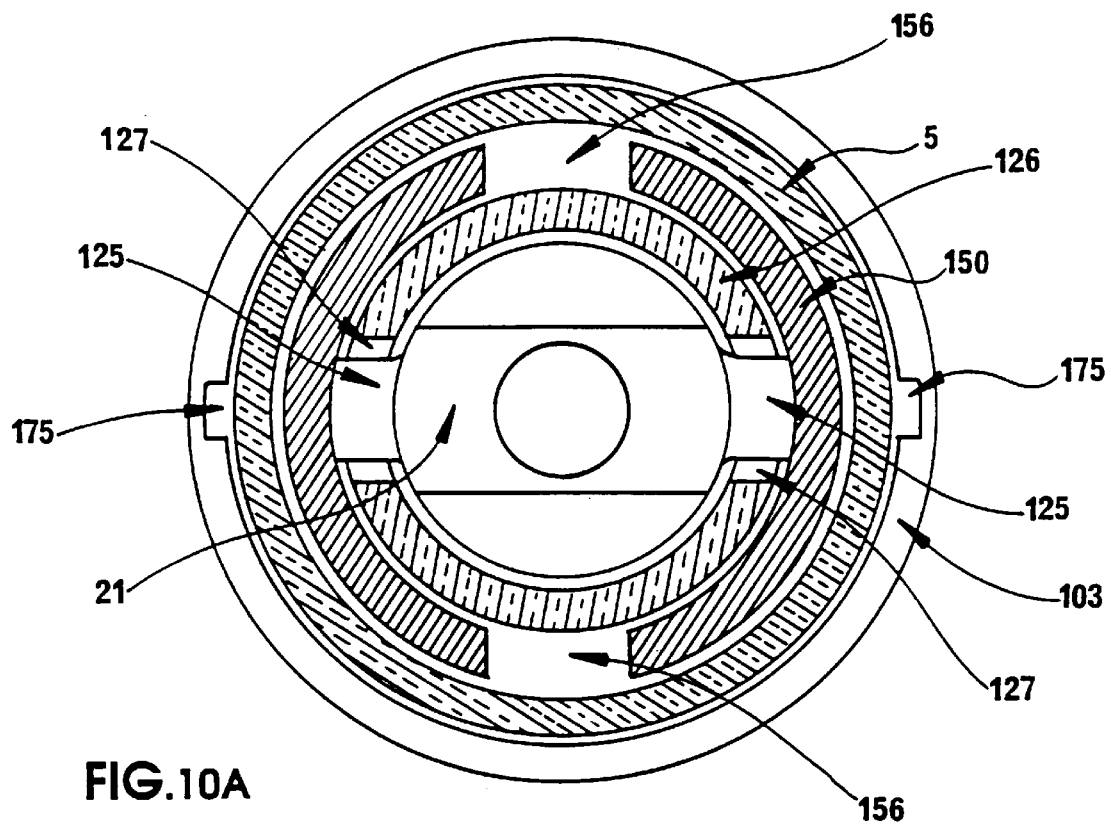
FIG. 10a is a horizontal section view from underneath on line I—I of FIG. 4, with the cocking member angularly positioned in the cocking position.
Figure 10B:
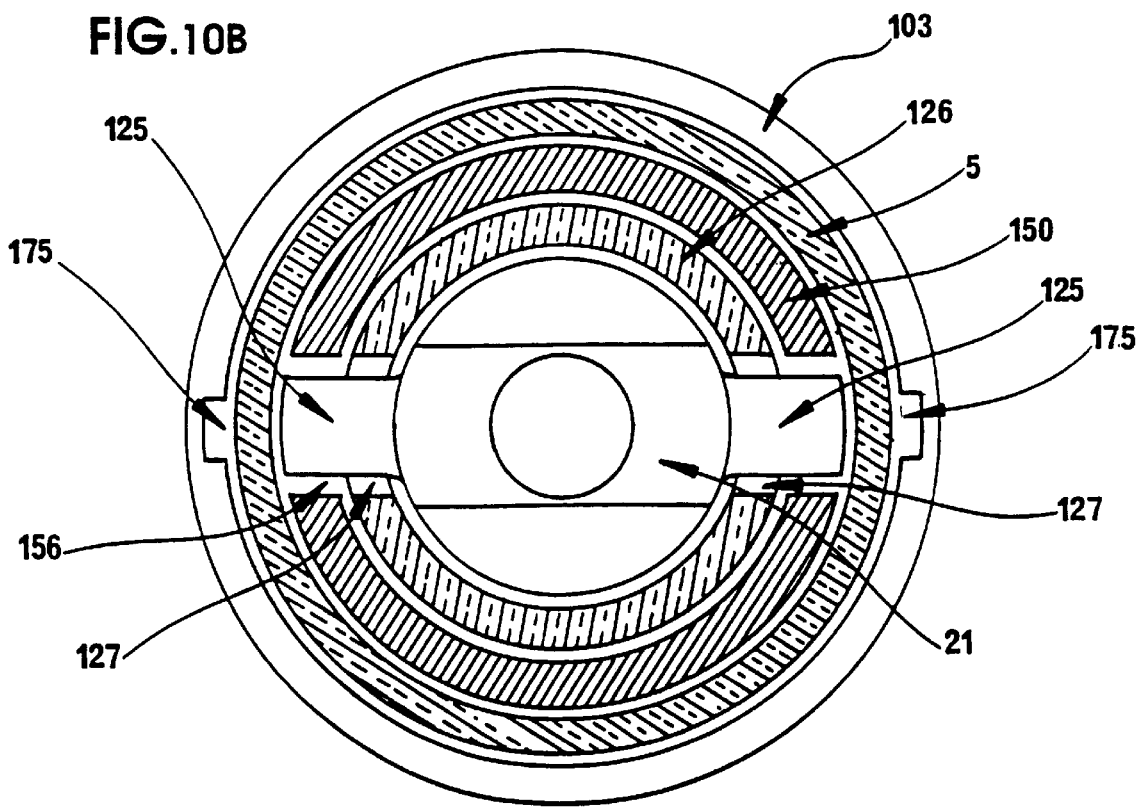
FIG. 10b is a horizontal section view from underneath on line II—II of FIG. 5, with the cocking member angularly positioned in the releasing position.

This is shown in particular in FIGS. 10a and 10b which are cross-section views of the auto-injector from underneath on lines I—I and II—II of FIGS. 4 and 5.

Figure 2:
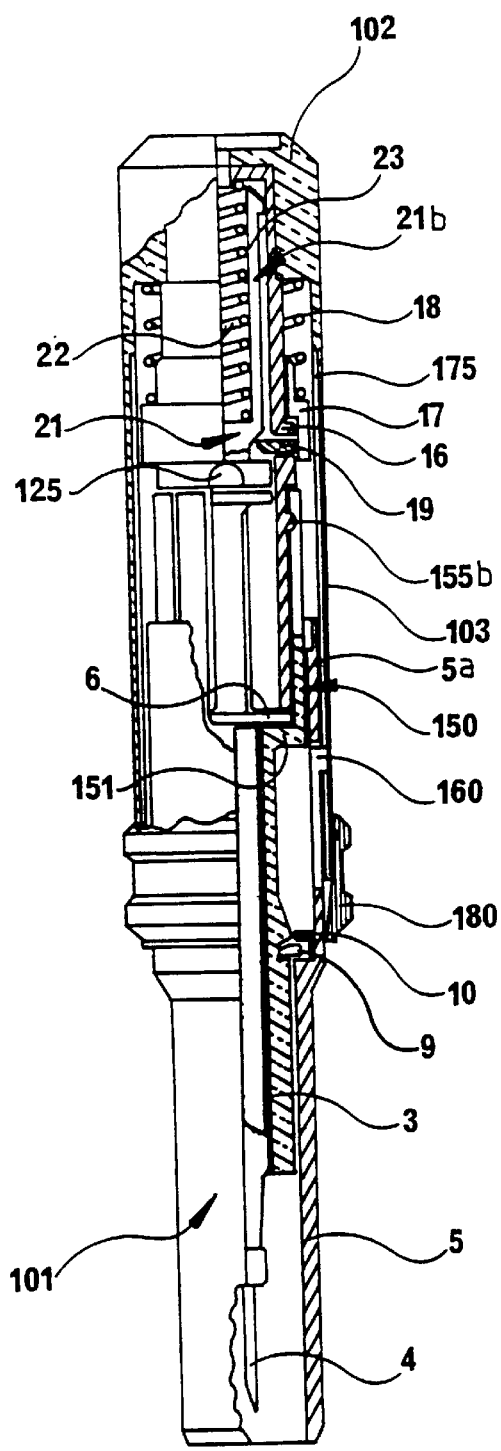
FIG. 2 is a view similar to the FIG. 1 view, before the automatic injection device is actuated.

When the cocking member 150 is in the releasing angular position (FIG. 10b), the fins 125 on the piston 21 are disposed facing the two axial slots 156 in the cocking member 150. This position is also shown in FIGS. 2 and 5 which show that the blocking tab 160 has penetrated into one of said two axial grooves 175 in the outer casing 103. As a result, the tube 5 is no longer prevented from being displaced on the cocking member 150, and the auto-injector can be actuated by applying it against that zone of the body into which the substance is to be injected. When the pressure is sufficient, the tube 5 slides over the cocking member 150 and the needle is uncovered, thereby penetrating into the body of the patient. When the tube 5 reaches its actuating position, its end 5a acts on the trigger means for triggering the injection device, as described above. The piston 21 is thus released, and it is displaced inside the fixed sleeve 126 towards its end-of-stroke position, its two fins 125 sliding in the two axial slots 127 of the fixed sleeve 126, and in the two axial slots 156 of the cocking member 150.

When the casing 103 is provided with two diametrically opposite axial grooves 175, and when the blocking finger 160 and the abutment finger 170 are disposed diametrically opposite each other on the tube 5, the abutment finger 170 also penetrates into one of said axial grooves 175 when the cocking member 150 is in its releasing angular position. The cover portion 102 is then secured to the housing portion 101 only via the securing groove 155A and via the securing rib 155b.

On actuating the auto-injector, the tube 5 slides on the cocking member 150 so that, at the moment when the end 5a of the tube 5 triggers the injection device, that portion of the tube 5 which is situated in the vicinity of the end 5a surrounds that portion of the cocking member 150 which is provided with said groove 155a. Thus, during operation of the injection device, the rib 155b cannot pop out of the groove 155a, and the cover portion 102 is thus held in fixed manner on the housing portion 101. The substance contained in the syringe 3 is then injected automatically into the body of the patient.

The end-of-stroke position of the piston 21 is shown in FIG. 3. The needle 4 of the auto-injector is then withdrawn from the body of the patient. Preferably, the tube 5 is provided with a return spring 8 which returns the tube 5 to its rest position in which it surrounds the needle 4. Simultaneously, the fastening between the cocking member 150 and the fixed sleeve 126 via the groove 155a and the rib 155b becomes releasable again. The housing portion 101 can thus be separated from the cover portion 102 merely by applying traction, the abutment finger 170 sliding in one of the axial grooves 175 of the casing 103, as shown in particular in FIG. 9b.

Once the housing portion 101 has been separated from the cover portion 102, either the syringe 3 only is replaced in the housing portion 101, and the auto-injector is recocked as described above, or the entire housing portion containing the empty syringe is replaced with another housing portion containing a new syringe. This second variant can be advantageous when it is not desirable for the user to use syringes other than those which are intended for said user.

In a variant of this first embodiment of the invention, it is possible to provide a window in the housing portion 101, making it possible to see the inside of said housing portion so as to check whether the syringe is present or absent. Furthermore, as shown in FIG. 3, a shoulder 110 projecting radially outwards from the housing portion 101 may advantageously be provided to facilitate the handling involved in opening and closing and thus in cocking the auto-injector.

FIGS. 11 and 14 show a second embodiment of a reusable auto-injector of the invention.

In the second embodiment, the auto-injector includes a substantially cylindrical housing 1, it being possible for the directrix of the cylinder to be arbitrary, e.g. circular or approximately rectangular. The housing 1 is provided with a cover 2 mounted to slide on said housing between a closed position and an open position in which the housing 1 and the cover 2 remain united. The syringe 3, the injection device for automatically injecting the substance contained in said syringe, and means for recocking said injection device are disposed inside the housing 1.

Unlike the above-described first embodiment, the auto-injector does not have two separable distinct portions, i.e. the housing portion and the cover portion remain permanently coupled together.

The automatic injection device is identical to that described above, like reference numbers designating like elements of the device. It is therefore only described below with respect to a variant embodiment of the trigger means shown in FIGS. 12 to 14 in relation to this second embodiment. It should however be noted that this variant can also be adapted to suit the above-mentioned first embodiment, and that the variant described for said first embodiment can also be adapted to suit the second embodiment.

Thus, as shown in FIGS. 12 and 14, the trigger means may be implemented in the form of at least one resilient tab that can bend either inwards or outwards, and whose free end is provided with a lug 20 acting as an interaction element. Advantageously, in this case, two identical resilient tabs 19 are provided diametrically opposite each other about the piston 21. For simplification purposes, implementation and operation of these two tabs are described below with reference to one tab only. The lug 20 of the tab 19 co-operates firstly, via its inside 20a, with the high portion 21b of the piston 21, and secondly, via its outside 20b, with the control sleeve 17. The smaller-diameter portion 21a co-operates with said lug 20 when the piston 21 is in the cocked position. In this position, the control sleeve 17, as urged by its spring 18, comes into abutment against a shoulder 16 of the housing, and it is then in its locking position in which it holds said lug 20 of said resilient tab 19 in its blocking position. The resilient tab 19 is thus subjected to the force exerted by the spring 22 on the piston 21. When the actuating member forces the control sleeve 17 into its unlocking position, the lug 20 is released on its outside 20b, and the tab 19 moves outwards under the effect of said force exerted by the spring 22 and/or of its own resilience, in a manner similar to that of the split ring in the first embodiment.

The piston 21 is then released and the product contained in the syringe is injected into the patient. The tab 19 is then in its piston-releasing position in which the outside 20b of said lug 20 holds the control sleeve 17 in its unlocking position. Said lug 20 is thus subjected to the force exerted by the spring 18 on the control sleeve 17. When the piston 21 returns to its cocked position and the lug 20 once again finds itself facing the smaller-diameter portion 21a of the piston 21, the tab 19 moves inwards under the effect of said force exerted by the spring 18 and/or of its own resilience.

As shown in FIG. 12 and in FIGS. 13 and 14, the tab 19 may either be bent outwards when it is in its releasing position in which it releases the piston 21 and be non-bent when it is in its blocking position in which it blocks the piston 21, or else be non-bent in its releasing position in which it releases the piston 21 and be bent inwards in its blocking position in which it blocks the piston 21.

In the former case, it is mainly the piston 21 that forces the tab 19 into its releasing position once the control sleeve 17 is in its unlocking position. In the latter case, it is mainly the control sleeve 17 that forces the tab 19 into its blocking position via its spring 18 once the lug 20 faces the smaller-diameter portion 21*a* of the piston 21.

In a manner identical to the first embodiment, the high portion 21*b* of the piston 21 advantageously comprises a hollow tubular cylinder 23 whose outside surface co-operates with the inside 20*a* of said lug 20. This cylinder 23 receives one end of the actuating spring 22, and it is provided with a frustoconical portion forming said smaller-diameter portion 21*a* of the piston 21 at that one of its ends which is closer to the syringe, i.e. its bottom end in the figures.

Implementing the smaller-diameter portion 21*a* of the piston 21 frustoconically ensures that the lug 20 slides progressively over said smaller-diameter portion 21*a* while the tab 19 is coming into or leaving its blocking position, thereby avoiding any risk of said tab 19 jamming in its blocking position.

Likewise, the control sleeve 17 may be similarly provided with a frustoconical portion where it co-operates with said lug 20 so as to avoid any risk of said tab 19 jamming in its releasing position in which it releases the piston 21.

In this second embodiment, shown in FIGS. 11 to 14, the recocking means comprise a telescopic element 50 connected firstly to the cover 2 and secondly to the piston 21. This telescopic element 50 includes an internal rod 52 which is secured to the high portion 21*b* of the piston 21. Preferably, as shown in FIGS. 13 and 14, the rod 52 is fixed to the end of said hollow cylinder 23 of the piston 21 and extends axially therein. It is thus an integral part of the high portion 21*b* of the piston 21.

The telescopic element 50 also includes a hollow external tube 51 fixed to the cover 2 by that one of its ends which is further from the syringe, e.g. by means of screw. The rod 52 is mounted to slide in the tube 51 between two abutment positions respectively corresponding to the cocked position and to the end-of-stroke position of the piston 21. Thus, when the piston is in its cocked position, the rod 52 is situated almost entirely inside the hollow tube 51, whereas when the piston 21 is in its end-of-stroke position, the rod is situated almost entirely outside said hollow tube.

At its end opposite from the end fixed to the cover, the hollow tube 51 is provided with retaining means, e.g. an annular projection 55 projecting into the tube and allowing the rod 52 to slide in the tube 51 until said projection reaches complementary means, e.g. an annular swelling 56, projecting outwards from the rod, and situated at that end of the rod 52 which is further from the syringe. Thus, the second abutment position of the rod 52, corresponding to the end-of-stroke position of the piston 21, is determined by said retaining means 55 on the tube 51, when they co-operate with said annular swelling 56 on said rod 52.

Both the tube 51, fixed to the cover 2, and the rod 52, fixed to the piston 21, can slide relative to the actuating spring 22. As shown in FIGS. 13 and 14, the spring 22 is disposed around said telescopic element 50, and it abuts firstly against the end of said cylinder 23 of the piston 21 and secondly against a fixed portion of the housing 1 of the auto-injector. The recocking device operates as follows. After the auto-injector has been used, the device is in the end-of-stroke position of the piston, as shown in FIG. 13. When the patient wishes to reload the auto-injector, the patient opens the cover 2 to uncover the syringe 3 in order to replace it. Advantageously, the above-mentioned resilient member 30 makes the syringe easier to grasp when the cover 2 is open.

Sliding the cover 2 to open it causes said cover to entrain with it the hollow tube 51 of the telescopic element 50. The tube 51 then slides inside the spring 22 while entraining the rod 52 with it by means of its annular projection 55 which co-operates with the annular swelling 56 on the rod. The rod 52 thus also slides inside the spring 22 and entrains the piston 21 with it, so that the syringe is released. The spring 22 pressing against the piston 21 via one of its ends is thus compressed during the operation of opening of the cover 2. Simultaneously, the piston 21 is progressively returned from its end-of-stroke position to its cocked position. Once the cover 2 is fully open, the smaller-diameter portion 21*a* of the piston 21 is situated level with the lug 20 of the at least one resilient tab 19. As a result, whereas during the entire movement of opening the cover 2, the lug 20 and the tab 19 co-operate with the outside surface of the cylinder 23 of the piston 21, once the cover is open, said tab 19 moves inwards to take up its blocking position in which it co-operates with said smaller-diameter portion 21*a*. Simultaneously, the tab 19 releases the control sleeve which then takes up its locking position under the effect of the force of the spring 18. The automatic injection device is thus recocked.

The user can then replace the empty syringe with a new syringe, and then close the cover 2. On closing the cover 2, the hollow tube 51 merely slides without resistance inside the spring 22 so as to be placed around the rod 52 as shown in FIG. 14. The auto-injector is then ready to be used again.

To make it easier to replace the syringe, a resilient member 30 may be provided acting on the syringe by urging it out of the housing 1 on opening the cover 2.

An example of such a resilient member is shown in FIGS. 15*a* and 15*b*. With reference to these figures, an opening 1*a* may be provided in the housing for the purposes of inserting and removing the syringe 3. To this end, a resilient member 30 advantageously implemented in the form of a resilient tongue is disposed between the syringe 3 and the wall of the housing opposite said opening 1*a*. The resilient tongue 30 is designed to slide in a recess 31 provided for this purpose between a closed position (FIG. 15*a*) in which the syringe is disposed inside the auto-injector with a view to operating said auto-injector, and an open position in which the syringe is urged out of the housing portion (FIG. 15*b*) via the opening 1*a* by means of the tongue 30. The tongue is displaced in the recess 31 between its open position and its closed position on opening and closing the cover 2.

What is claimed is:

1. A reloadable auto-injector comprising:

a syringe (3);

a housing portion (101) designed to receive the syringe (3);

a cover portion (102) which is removably attached to the housing portion; and an injection device for automatically injecting a substance contained in the syringe, said injection device comprising:

an actuating spring (22);

piston (21) comprising, in the vertical position of the auto-injector with the syringe (3) at the bottom, a high portion (21*b*) and a low portion (21*c*), said low portion (21*c*) co-operating with the plunger of the syringe, said piston (21) being mounted to move, under the effect of said spring (22) between a cocked position and an end-of-stroke position, said spring (22) being compressed in said cocked position; and trigger means (19) mounted to move between a blocking position in which said trigger means holds the piston (21) in its cocked position, and a releasing position in which said trigger means releases the piston (21), said trigger means (19) being released from the blocking position by an actuating member;

wherein said auto-injector further includes recocking means for recocking the automatic injection device, said auto-injector being characterized in that said recocking means include a cocking member (150) that co-operates with at least one element (125) secured to the piston (21) during the operation of closing said cover portion (102) in order to bring said piston (21) from its end-of-stroke position to its cocked position, said piston (21) sliding inside a fixed sleeve (126) in the cover portion (102) which includes at least one axial slot (127) through which said at least one element (125) secured to the piston projects, in order to cooperate with said cocking member (150).

2. An auto-injector according to claim 1, in which a control sleeve (17) is provided mounted to move between a locking position in which it holds the trigger means (19) in the blocking position and thus the piston (21) in its cocked position and an unlocking position in which said trigger means (19) comes into the releasing position in which said trigger means releases the piston (21), said control sleeve (17) being urged towards its locking position by a spring (18), and being forced into its unlocking position by said actuating member.

3. An auto-injector according to claim 2, in which said trigger means (19) is resilient, and is provided with an interaction element (20) co-operating on its inside (20a) with the high portion (21b) of the piston (21), and on its outside (20b) with the control sleeves (17), said interaction element (20) holding said control sleeve (17) in the unlocking position when said resilient trigger means (19) is in the releasing position in which said resilient trigger means (19) releases the piston (21), said high portion (21b) of the piston (21) including a smaller-diameter portion (21a) which co-operates with said interaction element (20) when the piston (21) is in its cocked position, so that said resilient trigger means (19) takes up the blocking position in which said resilient trigger means (19) blocks said piston (21), thereby simultaneously releasing said control sleeve (17) which takes up its locking position by coming into engagement around said interaction element (20) of said resilient trigger means (19), thereby preventing said trigger means from returning to the releasing position in which said resilient trigger means releases the piston (21), the piston (21) then being blocked in its cocked position.

4. An auto-injector according to claim 3, in which the high portion (21b) of the piston (21) comprises a hollow tubular cylinder (23) having an outside surface which co-operates with said interaction element (20) of said resilient trigger means (19), that end of said tubular cylinder (23) which is closer to the syringe being provided with a frustoconical portion forming the smaller-diameter portion (21a) of the piston (21), said tubular cylinder (23) receiving an end of said spring (22) for actuating the piston (21), the other end of said spring (22) being secured to the housing of the auto-injector, so that, on opening and/or on closing the cover portion (2, 102) of the auto-injector, said tubular cylinder (23) of the piston (21) slides inside said trigger means (19), thereby entraining the spring (22) so that it is compressed, until the smaller-diameter portion (21a) of the piston (21) co-operates with the interaction element (20) to block the piston (21) in its cocked position.

5. An auto-injector according to claim 4, in which said trigger means (19) is implemented in the form of at least one resilient tab, and said interaction element (20) is implemented in the form of a lug disposed at the free end of said resilient tab (19), said at least one resilient tab (19) being brought into its piston-releasing position whenever said control sleeve (17) is forced into its unlocking position, and said at least one resilient tab (19) being brought into its piston-blocking position under the effect of the force exerted by said control sleeve (17), whenever said interaction element (20) co-operates with said smaller-diameter portion (21a) of said piston (21).

6. An auto-injector according to claim 4, in which said trigger means (19) comprises a split ring (20) which takes up the piston-releasing position when the control sleeve (17) is forced into its unlocking position, and which takes up the piston-blocking position when the split ring (20) co-operates with the smaller-diameter portion (21a) of said piston (21).

7. An auto-injector according to claim 1, including a cover portion (102) that can be interfitted with the housing portion (101) by being fitted thereon, the injection device, for automatically injecting the substance contained in the syringe, being disposed in the cover portion (102), said cover portion (102) with said housing portion (101) on being closed bringing said piston (21) into its cocked position and bringing said trigger means (19) into the blocking position.

8. An auto-injector according to claim 7, in which said cover portion (102), and said housing portion (101) are generally cylindrical in shape, said cover portion (102) interfitting axially with said housing portion (101), said housing portion (101) including said recocking means which comprises said cocking member (150) that co-operates with said at least one element (125) secured to the piston on axially fitting said cover portion (102) onto said housing portion (101) so as to bring said piston (21) into its cocked position.

9. An auto-injector according to claim 8, in which said cocking member (150) in the housing portion (101) comes into engagement around said fixed sleeve (126) on fitting the cover portion (102) onto the housing portion (101), thereby acting on said at least one element (125) secured to the piston to bring said piston (21) into its cocked position.

10. An auto-injector according to claim 9, in which said cocking member (150) is cylindrical and is provided with at least one axial slot (156) to enable said at least one element (125) secured to the piston to slide relative to said cocking member (150) while the piston (21) is being displaced from its cocked position to its end-of-stroke position, it being possible for said cocking member (150) to be rotated about said fixed sleeve (126) between a cocking angular position, in which it co-operates with said at least one element (125) secured to the piston to cock said piston (21), and a releasing angular position, in which said at least one axial slot (156) in the cocking member (150) is disposed facing said at least one element (125) secured to the piston.

11. An auto-injector according to claim 10, in which said housing portion (101) includes a tube (5) mounted to slide axially relative to said cocking member (150) between a rest position in which it covers up the needle (4) of the syringe (3) and an actuating position in which it acts as an actuating member for actuating the injection device, its end (5a) further from the syringe releasing the trigger means (19) for triggering the injection means, said tube (5) being provided with blocking means (160) which prevents the tube (5) from being displaced axially on said cocking member (150) when said cocking member is in its cocking angular position, and which enables said tube to be displaced axially thereon, when the cocking member (150) is in its releasing angular position.

12. An auto-injector according to claim 11, in which said blocking means on the tube (5) is implemented in the form of a resilient blocking finger (160) projecting outwards from said tube (5), said tube (5) further including an abutment finger (170) projecting outwards from said tube (5), said abutment finger allowing the housing portion (101) to be separated from the cover portion (102) only when the cocking member (150) is in its releasing angular position.

13. An auto-injector according to claim 12, in which the cover portion (102) includes a cylindrical outer casing (103) which interfits with the tube (5) of the housing portion (101) by fitting around said tube, the inside diameter of said outer casing (103) being approximately identical to the outside diameter of said tube (5), so that said casing being interfitted with said tube forces said resilient blocking finger (160) inwards so as to prevent the tube (5) from being displaced axially relative to said cocking member (150), the open end of the casing (103) being provided with an insertion notch (165) for inserting said projecting blocking tab (160), said notch (165) being disposed circumferentially such that the cocking member (150) is disposed in its cocking angular position when the cover portion (102) is interfitted with the housing portion (101), the inside surface of the casing (103) being provided with at least one axial groove (175) extending to said open end, said at least one groove (175) being offset angularly relative to said notch (165) so that said blocking tab (160) penetrates into said at least one axial groove (175) when said cocking member (150) is in its releasing angular position.

14. An auto-injector according to claim 13, in which the inside surface of said cocking member (150) in the vicinity of the end thereof that co-operates with said at least one element (125) secured to the piston is provided with a securing circumferential groove (155a) which is releasably snap-fastened, after the piston (21) has been cocked, on a complementary circumferential rib (155b) provided on the fixed sleeve (126), said rib and groove (155a, b) securing the housing portion (101) to the cover portion (102) in a releasable manner before and after the auto-injector is actuated, and fixing the housing portion (101) to the cover portion (102) in a non-releasable manner while the auto-injector is being actuated, the end (5a) of the tube (5) blocking said groove on said rib when said tube (5) is in its actuating position.

15. An auto-injector according to claim 1, in which a resilient member (30) is provided urging said syringe (3) slightly out of the housing portion (101) of the auto-injector when the cover portion (102) is open, thereby making said syringe easier to grasp.

16. A reloadable auto-injector comprising:

a syringe (3);

a housing portion (1, 101) designed to receive the syringe (3);

a cover portion (2, 102) which is removably attached to the housing portion; and an injection device for automatically injecting a substance contained in the syringe, said injection device comprising:
    an actuating spring (22);
    a piston (21) comprising a high portion (21b) and a low portion (21c), said low portion (21c) co-operating with the plunger of the syringe, said piston (21) being mounted to move, under the effect of said spring (22) between a cocked position and an end-of-stroke position, said spring (22) being compressed in said cocked position; and
    a trigger mechanism (19) mounted to move between a blocking position in which said trigger mechanism holds the piston (21) in its cocked position, and a releasing position in which said trigger mechansim releases the piston (21), said trigger mechanism (19) being released from the blocking position by an actuating member;

wherein said auto-injector includes a recocking mechanism for recocking the automatic injection device, said recocking mechanism being organized to be actuated by an operation of opening and/or closing said cover portion (2, 102) of the auto-injector.

* * * * *